US006518011B1

(12) United States Patent
Seiffert et al.

(10) Patent No.: US 6,518,011 B1
(45) Date of Patent: Feb. 11, 2003

(54) METHOD FOR SCREENING COMPOUNDS TO IDENTIFY BETA-AMYLOID PRODUCTION MODULATORS

(75) Inventors: Dietmar A. Seiffert, Boothwyn, PA (US); Thomas J. Mitchell, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/481,980

(22) Filed: Jan. 12, 2000

Related U.S. Application Data

(60) Provisional application No. 60/115,749, filed on Jan. 13, 1999.

(51) Int. Cl.[7] .......................... C07K 1/00; C07K 14/00; C12N 15/00; C12Q 1/00
(52) U.S. Cl. .......................... 435/4; 435/7.1; 435/7.21; 435/69.1; 435/70.1; 435/320.1; 435/325; 530/300; 530/350
(58) Field of Search .............................. 435/4, 7.1, 7.9, 435/7.92, 69.1, 70.1, 320.1, 325, 252.3, 7.21; 530/300, 350

(56) References Cited

U.S. PATENT DOCUMENTS

| | | | |
|---|---|---|---|
| 4,666,829 A | 5/1987 | Glenner et al. | 435/6 |
| 5,593,846 A | 1/1997 | Schenk et al. | 435/7.9 |
| 5,766,846 A | * 6/1998 | Schlossmacher et al. | 435/6 |
| 6,245,884 B1 | * 6/2001 | Hook et al. | 530/300 |
| 6,284,221 B1 | * 9/2001 | Schenk et al. | 424/9.2 |

OTHER PUBLICATIONS

Haass et al. Polarized secretion of beta–amyloid precursor protein and amyloid beta–peptide in MDCK cells. Proc Natl Acad Sci 91: 1564–1568, 1994.*
Haass et al. Beta–amyloid peptide and a 3–kDa fregment are derived by distinct cellular mechanisms. J Biol Chem 268(5): 3021–3024, 1993.*
Koo et al. Evidence that production and release of amyloid beta–protein involves the endocytic pathway. J Biol Chem 269(26): 17386–17389, 1994.*
Bunnell et al. Gamma–secretase cleavage is distinct from endoplasmic reticulum degradation of the transmembrane domain of the amyloid precursor protein. J Biol Chem 273(48): 31947–31955, 1998.*
Jarvik et al. Epitope tagging. Annu Rev Genet 32: 601–618, 1998.*
Seiffert et al. Positive–negative epitope–tagging of beta amyloid precursor protein to identify inhibitors of beta amyloid processing. Molec Brain Res 84: 115–126, 2000.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome fucntion. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Seubert et al. Isolation and quantification of soluble Alzheimer's beta–peptide from biological fluids. Nature 359: 325–327, 1992.*
Seubert et al. Secretion of beta–amyloid precursor protein cleaved at the amino terminus of the B–amyloid peptide. Nature 361: 260–263, 1993.*
Simons et al. Intracellular routing of human amyloid protein precursor: axonal delivery followed by transport to the dendrites. J Neurosci Res. 41(1): 121–8, 1995.*
Paganetti et al. Amyloid precursor protein truncated at any of the gamma–secretase sites is not cleaved to beta–amyloid. J Neurosci Res. 46(3):283–93, 1996.*
Selkoe, D.J., 1994, Annu Rev. Cell Biol, 10, 373–403.
Glenner and Wong, 1984, Biochem. Biophys. Res. Commun. 120, 885–890.
Pike et al., 1993, J. Neurosci, 13, 1676–1687.
Goate et al., 1991, Nature, 349, 704–706.

\* cited by examiner

*Primary Examiner*—Gary L. Kunz
*Assistant Examiner*—Bridget Bunner
(74) *Attorney, Agent, or Firm*—Briana C. Buchholz; Rosemarie Wilk-Orescan

(57) ABSTRACT

The present invention is directed generally to methods and composition for monitoring the processing of epitope-tagged beta-APP. More specifically, the present invention relates to the use of such methods and composition for monitoring responses of cells expressing such epitope-tagged beta-APP or fragments thereof or cell free systems containing the epitope-tagged polypeptides to therapy of diseases associated with an altered metabolism of the beta amyloid precursor protein (APP), and for screening and evaluation of potential drugs for the treatment of these disorders, including Alzheimer's disease (AD).

7 Claims, 8 Drawing Sheets

METHOD FOR SCREENING COMPOUNDS TO IDENTIFY BETA-AMYLOID PRODUCTION MODULATORS

This application claims the benefit of U.S. Provisional Application No. 60/115,749 filed on Jan. 13, 1999.

FIELD OF THE INVENTION

This invention is directed to CDNA sequences, cell lines, and polypeptides containing epitope(s) for high-affinity antibodies within the A-beta fragment of the beta-amyloid precursor protein (beta-APP). A preferred embodiment of the invention relates to assays useful for identifying and characterizing beta amyloid precursor processing inhibitors, and for purifying APP processing enzymes. Such assays are useful in developing beta-APP processing modulators for the treatment of diseases associated with altered metabolism of beta-APP and an accumulation of amyloid A-beta.

BACKGROUND OF THE INVENTION

The present invention is directed generally to methods and compositions for monitoring the processing of epitope-tagged beta-APP. More specifically, the present invention relates to the use of such methods and compositions for monitoring responses of cells expressing such epitope-tagged beta-APP, or fragments thereof. The present invention also relates to cell free systems containing the epitope-tagged polypeptides, therapy of diseases associated with an altered metabolism of the beta-amyloid precursor protein (beta-APP), and for screening and evaluation of potential drugs for the treatment of these disorders, including Alzheimer's disease.

Alzheimer's disease (AD) is a degenerative brain disorder characterized clinically by progressive loss of memory, temporal and local orientation, cognition, reasoning, judgment and emotional stability. AD is a common cause of progressive dementia in humans and is believed to be one of the major causes of death in the United States. AD has been observed in all races and ethnic groups worldwide and presents a major present and future health problem. No treatment that effectively prevents AD, or reverses the clinical symptoms and underlying pathophysiology is currently known.

Histopathological examination of brain tissue obtained upon autopsy, or from neurosurgical specimens in affected individuals, revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments. Biochemical and immunochemical studies led to the conclusion that their principle protein subunit is an altered phosphorylated from of the tau protein (reviewed in Selkoe, D. J. Annu Rev Cell Biol 1994 10: 373–403).

Biochemical and immunological studies show that the dominant proteinaceous component of the amyloid plaque is a 4.2 kilodalton (kD) protein of from about 39 to about 43 amino acids in length. This protein was designated A-beta, beta-amyloid peptide, or beta/A4. In addition to its deposition in amyloid plaques, A-beta is also found in the walls of meningeal and parenchymal arterioles, small arteries, capillaries, and occasionally venules. A-beta was first purified and a partial amino acid sequence reported in 1984 (Glenner and Wong, Biochem. Biophys. Res. Commun. 120: 885–890). The isolation and sequence data for the first 28 amino acids are described in U.S. Pat. No. 4,666,829, the contents of which are herein incorporated by reference in their entirety.

Compelling evidence accumulated during the last decade revealed that A-beta is an internal polypeptide derived from a type 1 integral membrane protein, termed beta-APP. Beta-APP is normally produced by many cells both in vivo and in cultured cells derived from various animals and humans. A-beta is derived from cleavage of beta-APP by an as yet unknown enzyme (protease) system(s), collectively termed secretases. The existence of at least three proteolytic activities has been postulated. They include (a) beta secretase(s), generating the N-terminus of A-beta, (b) alpha secretase(s) cleaving in the region of the 16/17 peptide bond in A-beta, and (c) gamma secretases, generating C-terminal A-beta fragments ending at position numbers 38, 39, 40, 42, and 43. The precise biochemical mechanism by which A-beta is derived from beta-APP, and how it subsequently accumulates in cerebral tissue and blood vessels, is currently unknown.

Several lines of evidence suggest that the abnormal accumulation of A-beta plays a key role in the pathogenesis of AD. First, A-beta is the major protein found in amyloid plaques (Glenner G G, Wong, C W 1984 Biochem Biophys Res Commun 120: 885–90). Second, A-beta is neurotoxic and may be causally related to neuronal death observed in AD patients (Pike C J, Burdick, D, Walencewicz A J, Glabe C G, Cotman C W 1993 J Neurosci 13: 1676–87). Third, missense DNA mutations at position 717 in the 770 isoform of beta-APP can be found in affected members but not in unaffected members of several families with a genetically determined (familial) form of AD (Goate A, Chartier-Harlin M-C, Mullan M, Brown J, Crawford F et al 1991 Nature 349: 704–6). In addition, several other beta-APP mutations have been described in familial forms of AD (reviewed in Selkoe D J 1994 Annu Rev Cell Biol 1994 10: 373–403). Fourth, similar neuropathological changes have been observed in transgenic animals overexpressing mutant forms of human beta-APP (Hsiao K, Chapman P, Nilsen S, Eckman C, Harigaya Y, Younkin S, Yang F, Cole G 1996 Nature 274: 99–102). Finally, individuals with Down's syndrome have an increased gene dosage of beta-APP and develop early-onset AD. Taken together, these observations strongly suggest that A-beta depositions may be causally related to Alzheimer's disease.

While large progress has been made in understanding the underlying cause(s) of AD and other A-beta related diseases, there remains a need to develop methods and compositions for the treatment of the disease(s). Treatment methods could be based on compounds that inhibit the formation of A-beta in vivo. To identify and characterize such compounds, high-throughput screening methods are required to identify compounds that affect beta-APP processing. Specific assays for A-beta detection should be able to detect A-beta in biological samples at very low concentrations, as well as distinguishing between A-beta and other fragments of beta-APP that may be present in the sample.

U.S. Pat. No. 4,666,829, suggests the use of an antibody to the 28-amino acid fragment of A-beta to detect "Alzheimer's Amyloid Polypeptide" in biological samples. This suggestion was not used in the present invention.

Several attempts to measure A-beta in biological samples by immunological methods have been reported. While these studies detect very low levels of A-beta peptides, no attempts to purify and characterize this immunoreactivity further and to determine whether it indeed represents A-beta have been reported.

U.S. Pat. No. 5,593,846 describes assays aimed at determining A-beta levels in biological samples using antibodies based on the native A-beta sequence. No attempt was made to differentiate between A-beta peptides with heterogenous C-termini by either enzyme-linked immunosorbant assay (ELISA), or radioimmunoassay (RIA). More specifically, the assay system described therein is based on antibodies that recognize epitopes in the A-beta polypeptide between amino acids 1 to 28 of A-beta, and does not differentiate between A-beta (1–40) and A-beta (1–42). In addition, the assay is not anticipated to be sufficiently sensitive to detect the levels of A-beta (1–42) that are expected to accumulate in beta-APP transfected mammalian cells in the 96-well microtiter plate format required for high-throughput drug screening.

While mutations have been introduced within the A-beta sequence of beta-APP (for example Citron M, Teplow D B, Selkoe D J 1995 Neuron 14:661–670), the use of beta-APP molecules epitope-tagged within the A-beta sequence has not been explored.

SUMMARY OF THE INVENTION

The present invention provides methods that enable one skilled in the art to identify and characterize beta amyloid production inhibitors. Recombinant expression constructs were prepared containing an epitope for a high-affinity antibody centered about the alpha secretase cleavage site of the A-beta fragment of the beta-APP. Cell lines were established that express these mutant forms of beta-APP and secrete fragments of epitope-tagged beta-APP. In addition, epitope-tagged beta amyloid fragments were also prepared by chemical synthesis.

An object of the invention provides assays and methods for the detection and characterization of epitope-tagged beta-APP and fragments thereof. The invention provides enzyme-linked immunosorbent assays (ELISA) and other immunological methods suitable for the detection of alpha, beta, and gamma secretase modulators in cell-based and cell-free assay systems. An accumulation of epitope-tagged A-beta was observed in cells transfected with the expression cassette. The cultured cells were exposed to test compounds that cause a change in the secreted amount of soluble epitope tagged fragments of beta-APP. The present assays and methods may be used to identify beta amyloid precursor processing modulators and to develop therapeutic modalities based on modification of beta amyloid precursor processing.

Panel A: Microtiter wells were coated with mAB anti-HA 11 and after blocking, incubated with a dose-response of a synthetic HA 11 A-beta (1–40) peptide containing the HA 11 epitope centered on the alpha secretase cleavage site. Bound A-beta HA 11 was detected with polyclonal antibodies specific for position 1 (Serotec) or position 40 (QCB), followed by HRP-labeled anti-rabbit IgG and TMB substrate. The change of absorbance at 650 nM was monitored and results are corrected for binding of secondary antibodies to wells not incubated with the A-beta HA 11 peptide. Results are expressed as change of absorbance per minute (mOD/minute).

Panel B: Microtiter wells were coated as in panel A and incubated with the indicated dilutions of HEK 293/HA 11 beta-APP 695 conditioned medium (24 hours). Bound HA 11 beta-APP 695 fragments were detected with antibodies specific for position 1 and 40 as in panel A. Results are expressed and corrected as in panel A.

Figure 5:
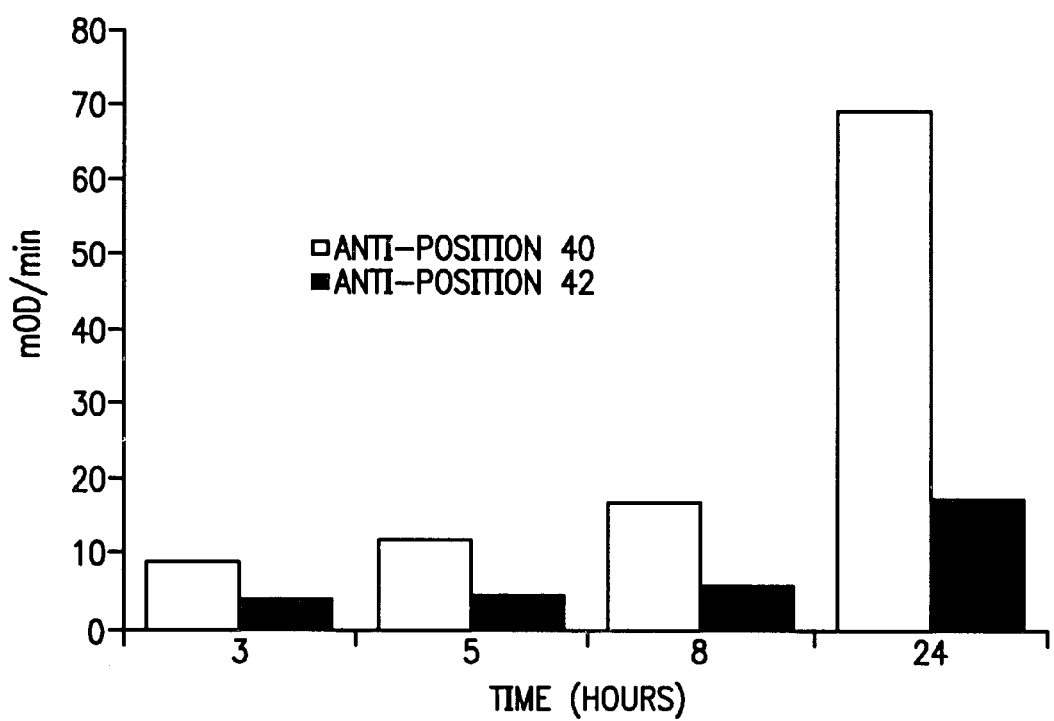

FIG. 5 Shows a time-course of the accumulation of HA 11 A-beta (1–40) and A-beta (1–42) in HEK 293/HA 11 beta-APP 695 conditioned medium. HEK 293/HA 11 beta-APP 695 was cultured in serum-free medium containing 0.2% bovine serum albumin in 96-well microtiter plates for the indicated time intervals. The accumulation of HA 11 A-beta (1–40) and A-beta (1–42) was determined. For HA 11 A-beta polypeptides ending at position 40, microtiter wells were coated with mAB anti-HA 11 and bound polypeptides were detected with rabbit anti-A-beta 40 (QCB), followed by HRP-labeled anti-rabbit IgG. For the position 42-specific ELISA, microtiter wells were coated with mAB anti-HA 11, and bound polypeptides were detected with biotin-labeled mAB 108 (position 42-specific), followed by streptavidin-HRP conjugate. Results are corrected for binding of secondary antibodies in the absence of conditioned medium and expressed as change of absorbance at 650 nM per minute (mOD/minute).

Figure 6A:
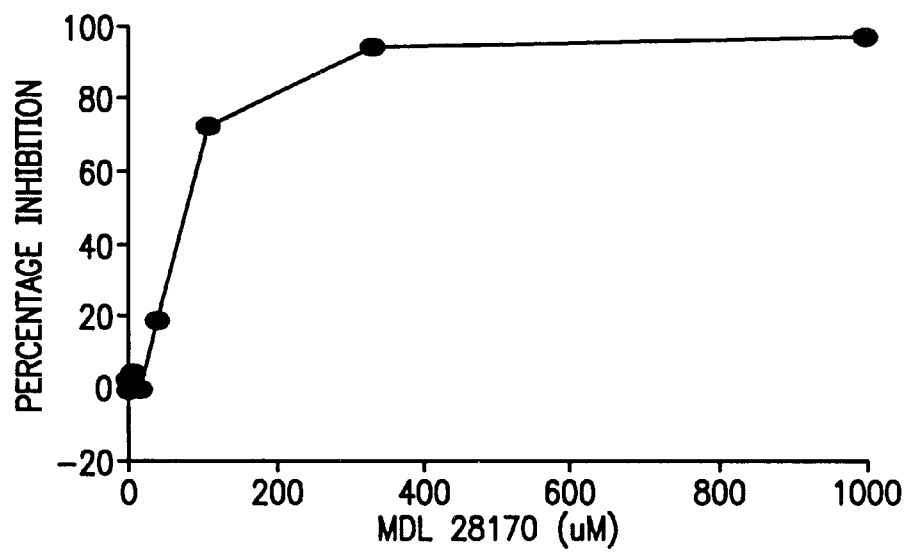
Figure 6B:
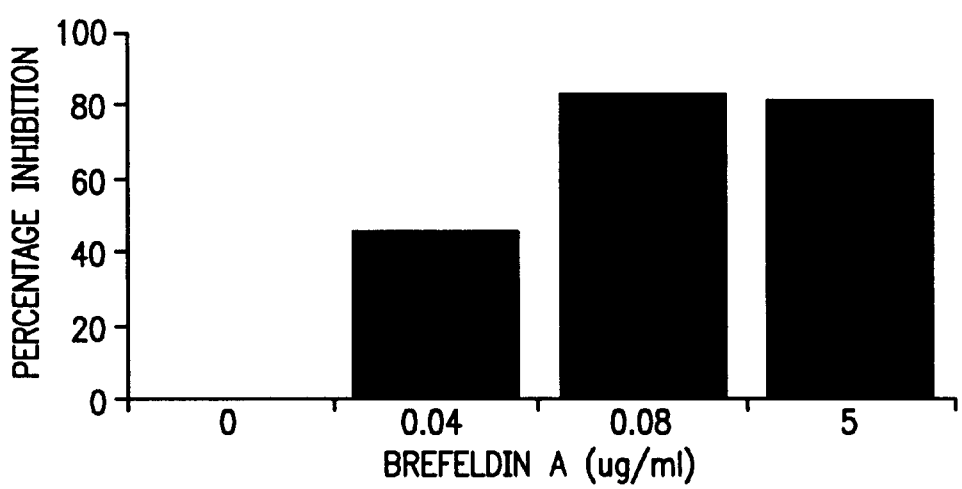

FIG. 6 Shows the effect of MDL 28170 and Brefeldin A on the accumulation of HA 11 A-beta (1–40) in HEK 293/HA 11 beta-APP 695 conditioned medium. HEK 293/ HA 11 beta-APP 695 cells were plated at confluence in 96-well plates and the indicated dose-response of either MDL 28170 (panel A), or Brefeldin A (panel B) was added for 16 hours. The accumulation of HA 11 A-beta (1–40) (position 40-specific antibody; QCB) was determined as in FIG. 5. Results are expressed as percentage inhibition of HA 11 A-beta (1–40) accumulation in comparison to wells incubated with vehicle (dimethyl sulfoxide, DMSO) alone.

Figure 7A:
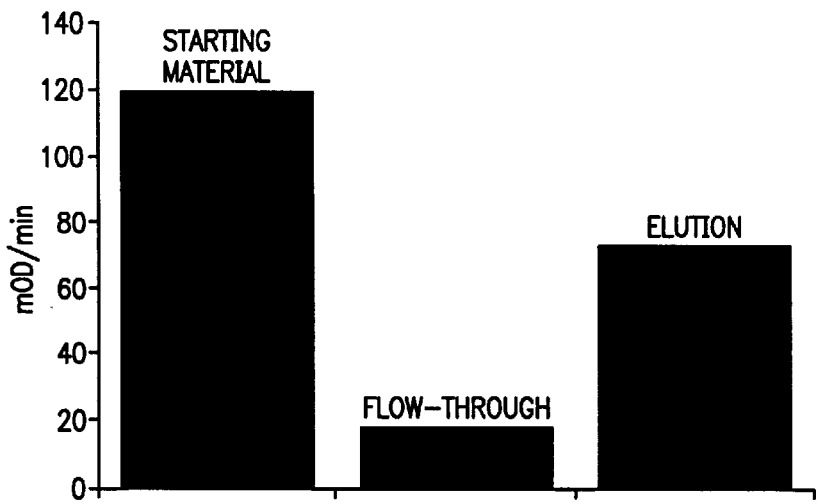
Figure 7B:
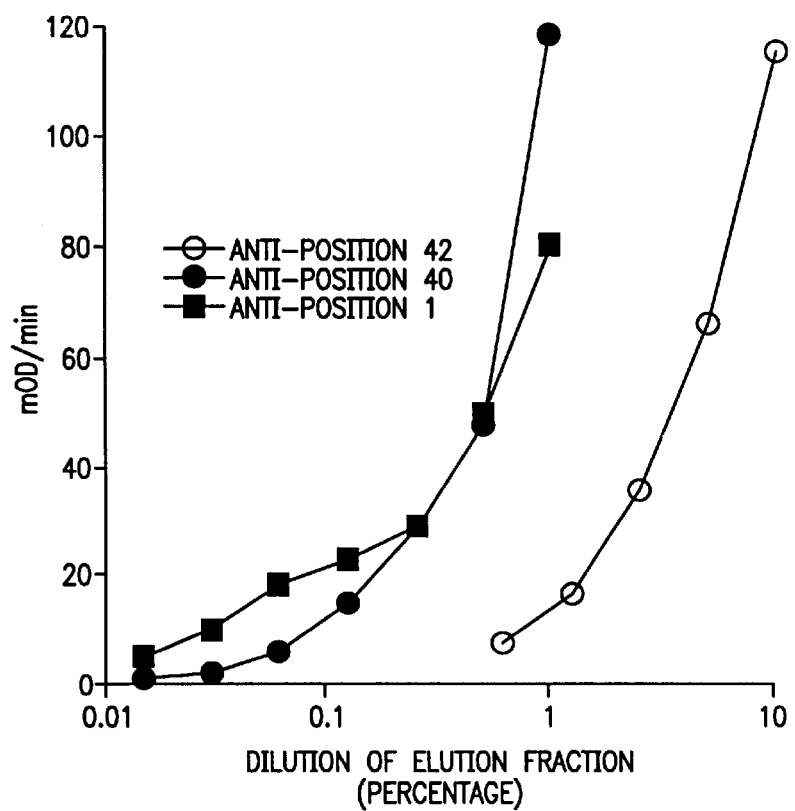
Figure 7C:
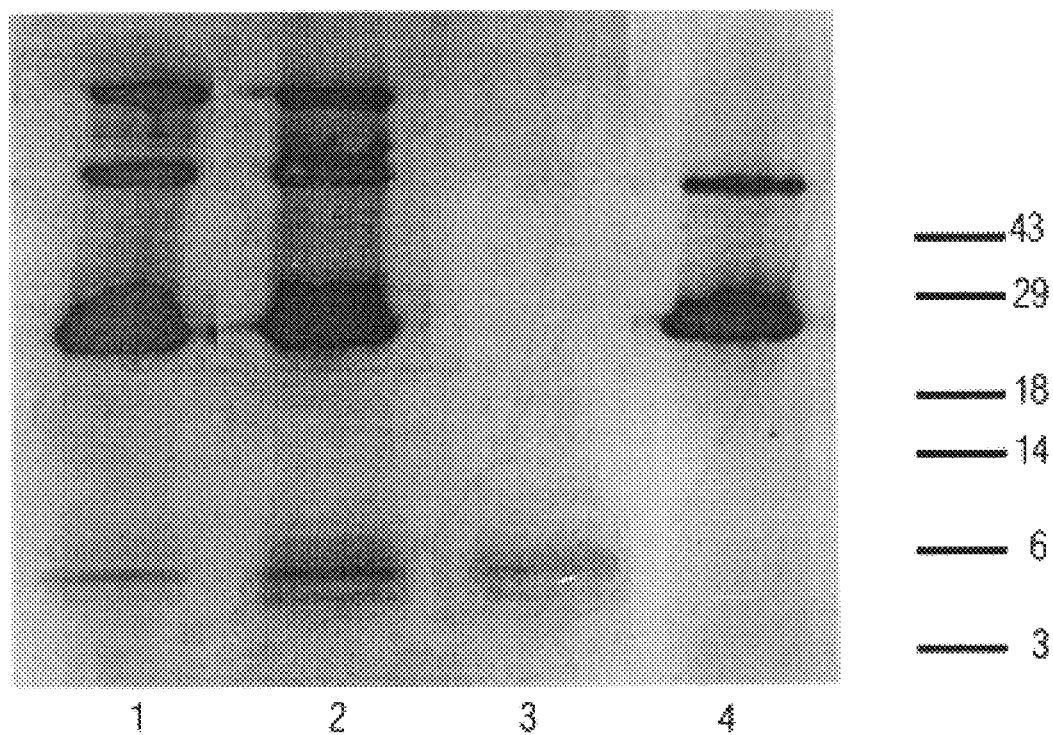

FIG. 7 Shows an isolation of HA 11 A-beta from HEK 293/HA 11 beta-APP 695 cells. Conditioned medium (serum-free containing 0.2% BSA) was passed over an mAB anti-HA 11 affinity matrix. After washing, the column was eluted with 5% formic acid in water. The peak fractions were pooled, dried in a Speed-Vac, resuspended in water and the pH was adjusted to 7.4 with Tris.

Figure 4A:
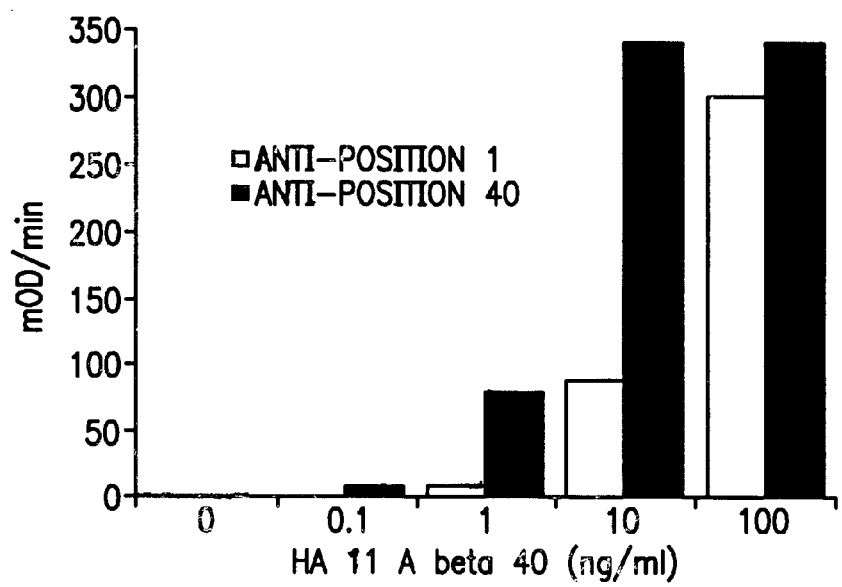
FIG. 4 Shows the detection of epitope-tagged beta-APP fragments in HEK 293 conditioned medium after transfection with HA 11 beta-APP 695.
Figure 4B:
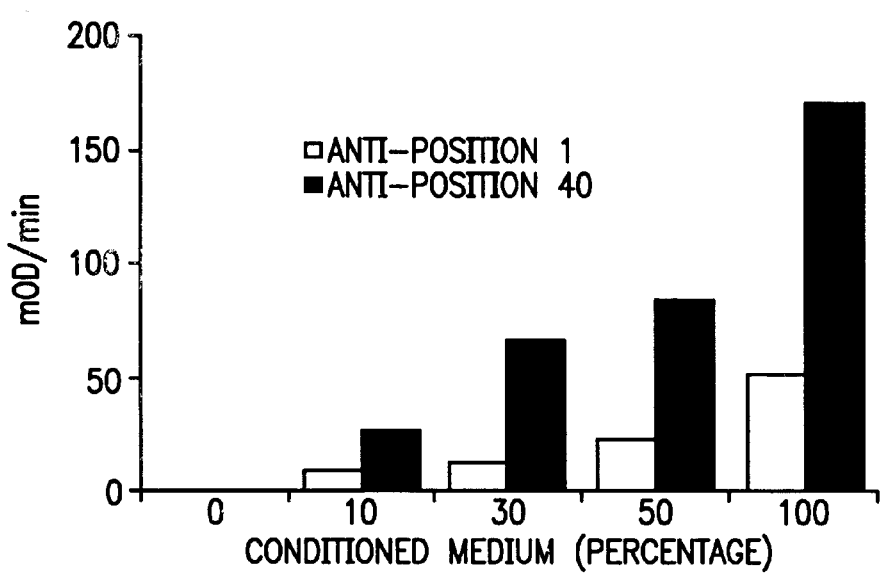

Panel A: The starting material, flow-through, and the pooled elution fractions (after dilution to account for the concentration of the HA 11 A-beta on the column) were analyzed by ELISA specific for position 40 in HA 11 A-beta as in FIGS. 4 and 5.

Panel B: The indicated dilutions of the pooled elution fractions were analyzed by ELISA specific for position 1, 40, and 42 in HA 11 A-beta. Note that approximately equal immunoreactivity is present for the position 1 and 40 antibodies, whereas the 42-specific reactivity is lost with 10-fold lesser dilution.

Panel C: The elution fractions were analyzed by SDS-PAGE (16.5% polyacrylamide in separating gel), followed by immunoblotting with mAB anti-HA 11, followed by HRP-labeled anti-mouse Ig, and chemiluminescence detection (ECL™, Amersham). Lane 1, elution fraction, stained with mAB anti-HA 11; lane 2, elution fraction spiked with HA 11 A-beta peptide (50 ng); lane 3, purified A-beta HA 11 1–40 peptide; and lane 4, elution fraction, stained under omission of anti-HA 11.

DETAILED DESCRIPTION OF THE INVENTION

The practice of the present invention generally employs conventional techniques of molecular biology, microbiology, recombinant DNA, and immunology, which are within the skill of the art. Such techniques are explained fully in the literature. See for example J. Sambrook et al., "Molecular Cloning; A Laboratory Manual" (1989); "DNA Cloning", Vol. I and II (D. N. Glover ed., 1985); "Oligonucleotide Synthesis" (M. J. Gait ed., 1984); "Nucleic Acid Hybridization" (B. D. Hames and S. J. Higgins eds., 1984); "Transcription and Translation" (B. D. Hames & S. J. Higgins eds., 1984); "Animal Cell Culture" (R. I. Freshney ed., 1986); "Immobilized Cells and Enzymes" (IRL Press, 1986); "A Practical Guide to Molecular Cloning" (B. Perbal, 1984); the series, "Methods in Enzymology" (Academic Press, Inc.); "Gene Transfer Vectors for Mammalian Cells" (J. H. Miller and M. P. Calos eds., 1987, Cold Spring Harbor Laboratory); *Meth. Enzymol.* (1987) 154 and 155 (Wu and Grossman, and Wu eds., respectively); "Immunochemical Methods in Cell and Molecular Biology" (Academic Press, London); "Protein Purification: Principles and Practice", Third Ed. (Scopes, Springer-Verlag, N.Y., 1994); and "Handbook of Experimental Immunology", Volumes I–IV (Weir and Blackwell, eds., 1986).

The present invention results from the discovery that the A-beta sequence of the beta-APP can be modified by inclusion of an epitope tag for a specific monoclonal antibody without apparent loss of proteolytic cleavage by secretases and/or related enzyme systems. In particular, it has been found that such epitope-tagged A-beta peptides are generated by cultured mammalian cells and may be measured in the conditioned medium.

A preferred embodiment of the invention provides methods and compositions for the detection of epitope-tagged beta-APP processing modulators useful for the treatment of diseases associated with altered metabolism of beta-APP. The method relies on the measurement of a very low concentration in a fluid sample, typically in the range from 0.05 ng/mL to 10 ng/mL, with the present invention providing highly sensitive and specific methods for performing such measurements. In particular, detection methods of the present invention provide for measurement of HA 11 A-beta at concentrations of 0.1 ng/mL and below, and are sufficiently sensitive and specific to distinguish HA 11 A-beta polypeptides with a C-terminal ending at position 40 or 42. This discovery is exemplified by the detection of both HA 11 A-beta 40 and 42 in a 96-well tissue culture format. In addition, the suitability of the invention for the identification of secretase inhibitors is exemplified by the inhibition of HA 11 A-beta 40 accumulation in the presence of a reported secretase inhibitor (MDL 28170; Mehdi S, Angelastro M R, Wiseman J S, Bey P, 1988 Biochem Biophys Res Commun 157, 1117–1123), and agents that interfere with the secretory pathway (Brefeldin A). Thus, these examples indicate that the assays of the invention are suitable for use in high-throughput screening for the detection of secretase inhibitors.

The terms and abbreviations used herein have their normal meanings unless otherwise designated. For example, "° C." refers to degrees Celsius; "N" refers to normal or normality; "mmole" refers to millimole or millimoles; "g" refers to gram or grams; and "M" refers to molar or molarity.

All amino acid or protein sequences, unless otherwise designated, are written commencing from the amino terminus ("N-terminus") and concluding with the carboxy terminus ("C-terminus").

All nucleic acid sequences, unless otherwise designated, are written in the direction from the 5' end to the 3' end, frequently referred to as "5' to 3'". The abbreviations A,C,G, and T correspond to the 5'-monophosphate forms of the deoxyribonucleosides deoxyadenine, deoxycytidine, deoxyguanine, and deoxythimine respectively, when they occur in DNA molecules.

The term "digestion" or "restriction" of DNA refers to the catalytic cleavage of the DNA with a restriction enzyme that acts only at certain sequences in the DNA molecule. The various restriction enzymes used herein are commercially available and their reaction conditions, cofactors, and other requirements were used as would be known to one of ordinary skill in the art.

The term "plasmid" refers to an extrachromosomal (usually) self-replicating genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "expression vector", as used herein, refers to any recombinant DNA cloning vector in which a promoter has been incorporated.

The term "promoter" refers to a DNA sequence that directs transcription of DNA to RNA.

The term "transcription", as used herein, refers to the process whereby information contained in a nucleotide sequence of DNA is transferred to a complementary RNA sequence.

The term "transfection", as used herein, refers to the taking up of an expression vector by a host cell, whether or not any coding sequences are in fact expressed. Numerous methods for transfection are known to the ordinarily skilled artisan, for example, calcium phosphate co-precipitation, lipofection, and electroporation. Successful transfection is generally recognized when any indication of the operation of this vector occurs within the host cell. Other routes of production are well known to skilled artisans. In addition to the plasmid described, it is well known in the art that some viruses are also appropriate vectors.

The term "neo-epitope", as used herein, refers to an antibody binding site (epitope) that is only weakly or not expressed in the intact polypeptide chain. Exo- and/or endoproteolytic cleavage of the polypeptide chain increases the affinity of the antibody for the epitope on the polypeptide chain. "Epitope tag" refers to an epitope for an antibody that is not naturally present in a polypeptide chain. It typically contains a defined polypeptide sequence of from about 5 to about 15 amino acids that can be inserted into a naturally occurring or otherwise generated larger polypeptide.

The term "polyclonal antibody", as used herein, refers to a population of heterogeneous antibodies derived from multiple clones, each of which is specific for one of a number of determinants found on an antigen. Serum obtained from immunizing suitable vertebrate hosts with polypeptide sequences. "Monoclonal antibody" refers to antibodies derived from an immortalized cell line capable of producing antibodies having desired specificity. "Capture antibody", as used herein, refers to an antibody that is linked to a solid-phase matrix in a biologically active form. A number of procedures for the immobilization of antibodies are known in the art, including passive absorption to plastic surfaces and chemical cross-linking. "Binding substance", as used herein, refers to an antibody capable of binding to an epitope in a polypeptide chain.

The term "solid-phase", as used herein, refers to a surface that is capable of binding a polypeptide chain. A number of solid-phase surfaces are known in the art including, but not limited to, plastic surfaces and agarose beads.

As used herein, the term "recombinant expression system" refers to a strong promoter encoding sequence, a strong ribosome binding site, a DNA sequence encoding a naturally-occurring or otherwise generated DNA sequence, a selectable marker encoding sequence, and a polyadenylation signal encoding sequence. Upon transferring this recombinant expression system into a suitable organism, it drives the production of a desired protein molecule. "Recombinant expression construct", as used herein, is any DNA, whether naturally-occurring or otherwise from any source that is capable of being inserted into any organism and drives the production of a desired protein molecule over a desired time frame.

The term "cDNA construct", as used herein, refers to a nucleic acid sequence, whether naturally-occurring or otherwise, from any sources than can be replicated in a desired organism.

The terms "A-beta 40, A-beta 42", as used herein, refer to a polypeptide fragment of beta APP which contains all or parts of sequence ID NO:1 with a c-terminal ending at position 40 (Val-Gly-Gly-Val-Val-COOH), or ending at position 42 (Val-Gly-Gly-Val-Val-Ile-Ala-COOH).

The term "A-beta", as used herein, refers to an amino acid fragment, approximately 39 to 43 amino acids in length, of a large transmembrane glycoprotein referred herein as beta-APP. Beta-APP is encoded by a gene on the long arm of human chromosome 21. The 43-amino acid sequence of A-beta is listed below:

$NH_2$-ASP ALA GLU PHE ARG HIS ASP SER GLY TYR GLU VAL HIS HIS GLN LYS LEU VAL PHE PHE ALA GLU ASP VAL GLY SER ASN LYS GLY ALA ILE ILE GLY LEU MET VAL GLY GLY VAL VAL ILE ALA THR-COOH (SEQ ID NO:1).

The term "epitope-tagged A-beta", as used herein, refers to a polypeptide sequence containing the above sequence (sequence ID NO:1) with the substitution and/or insertion of specific amino acids comprising the epitope (i.e., antibody recognition site) of a high-affinity antibody.

The term "beta-APP" refers to a polypeptide that is encoded by a gene of the same name localized in humans on the long arm of chromosome 21, and which includes the A-beta sequence within its C-terminal region sequence. Beta-APP is a single membrane-spanning, glycosylated protein expressed in a number of mammalian cells. Examples of specific isoforms of beta-APP that are currently known to exist in humans are the 695 amino acid polypeptide (Kang J, Lemaire H, Unterbeck A, Salbaum J M, Masters C L et al 1987 Nature 325: 733–36), the 751 amino acid form described by Ponte et al 1988 (Nature 331: 525–27), and the 770 amino acid polypeptide described by Kitaguchi et al 1988 (Nature 331: 530–32). Examples of specific variants of beta-APP include point mutations that can differ in both position and phenotype (reviewed in: Selkoe D J 1994 Annu Rev Cell Biol 10: 373–403). The skilled artisan will recognize that the epitope tagged A-beta sequence can be included in any of these splice variants or mutated beta-APP molecules.

The term "beta-APP fragment", as used herein, refers to fragments of beta-APP other than those that solely consist of A-beta (i.e., sequence ID NO:1). Beta-APP fragments include amino acid sequences of beta-APP in addition to those that comprise the A-beta polypeptide.

The term "conditioned media" refers to the aqueous extracellular fluid that surrounds cells grown in tissue culture (in vitro) and consists of, but is not limited to, proteins, polypeptides, and amino acids secreted by the cells.

The term "body fluid" refers to those fluids of a mammalian host that are expected to contain measurable amounts of epitope tagged A-beta or beta-APP fragments and include, but are not limited to, cerebrospinal fluid, blood, peritoneal fluid, and urine.

The term "blood", as used herein, includes but is not limited to, whole blood, plasma, serum, and the cellular components present in blood.

The term "small molecule", as used herein, refers to chemical compositions having a molecular weight less than approximately 900 g/mole.

The term "biological polymer", as used herein, refers to a macromolecule occurring in a living organism including, but not limited to, peptides, proteins, polysaccharides, or nucleic acids.

The term "splice variant", as used herein, refers mRNA molecules that have variant sequences due to the phenomenon of alternative splicing. Alternative splicing occurs when some introns of certain genes are not spliced out of some of the RNA molecules, leaving new combinations of exons. Splice variants also include mRNA molecules whose variant sequences arise from splicing that occurs within the exon. When different splicing possibilities exist at several positions of the transcript, a single gene can produce dozens of different proteins.

The term "production modulator", as used herein, refers to compounds which inhibit A-beta peptide release and/or its synthesis, and accordingly, have utility in treating Alzheimer's Disease.

The term "processing activities", as used herein, refers to cellular activity that results in the formation and/or release of A-beta peptides.

The term "competitive binding", as used herein, refers to a situation in which one substance competes with another substance for a binding site on a third substance.

Skilled artisans will recognize that the proteins of the present invention can be synthesized by a number of different methods. All of the amino acid compounds of the invention can be made by chemical methods well known in the art, including solid-phase peptide synthesis, or recombinant methods.

Practitioners of this invention realize that, in addition to the above mentioned expression systems, the cloned cDNA may be utilized in the production of transgenic animals, usually a mouse, in which expression or overexpression of the proteins of the present invention can be assessed.

Skilled artisans will recognize that the function of the amino acid composition will not be affected by alterations in the epitope-tagged A-beta sequence. For example, some hydrophobic amino acids may be exchanged for other hydrophobic amino acids. Those altered amino acid compositions that confer substantially the same function in substantially the same manner as the exemplified amino acid composition are also encompassed within the present invention. Although a preferred embodiment of this invention indicates the location of the epitope tag is centered around the alpha secretase cleavage site of A-beta, the skilled artisan will recognize that the epitope tag may also be placed in other locations in A-beta (1–42), or the 20 amino acids flanking either of the N-terminal or C-terminal regions. Furthermore, it is well known in the art that besides the HA 11 epitope used in this invention, a number of different epitope tags may be used. Examples include the inclusion of the myc epitope and the flag epitopes.

According to the present invention, epitope-tagged A-beta and beta-APP fragments may be detected and quantified in a variety of biological samples. Biological samples also include in vitro samples such as conditioned medium from cultured cells, transfected cell lines, and endogenous cell lines derived from transgenic animals. In vivo samples (i.e., body fluids) derived from transgenic animals may also be analyzed. Detection and quantification may be accomplished by any technique capable of distinguishing epitope-tagged A-beta, or fragments thereof, from other beta-APP fragments that can be found in the sample. Immunological techniques can be employed using binding substances specific for epitope-tagged A-beta and other sequences within A-beta, including but not limited to antibodies, antibody fragments, and recombinant antibodies, which bind specifically, and with high sensitivity, to epitope-tagged A-beta. Particularly suitable detection techniques include, but are not limited to, ELISA, immunoblotting, and radioimmunoassay (RIA).

A preferred immunoassay technique of the present invention is a two-site or "sandwich" assay. This assay utilizes an epitope tag specific antibody and a second antibody that binds to an epitope other than that bound by the first capturing antibody. The skilled artisan knows that the order of capturing and detecting antibody may be changed, and that one of the antibodies may be labeled with radioisotopes, enzymes, biotin, streptavidin, or a similar substituent. Alternatively, if different immunoglobulin fragments or species for antibody production were utilized for the generation of antibodies, secondary labeled antibodies specific for the detection antibody may be used. Illustrations of these approaches are described in the Example section.

In the present invention immunological techniques may be combined with physical separation methods. For example, gel electrophoresis may be used to separate complex biological samples containing epitope-tagged beta-APP molecules, and/or fragments thereof, by size and/or charge differences. The gels may then be probed by immunoblotting or a similar technique to identify specific polypeptides based on size or charge. This approach is illustrated in the following Example section.

A preferred embodiment of the present invention is cell lines capable of expressing epitope-tagged beta-APP, or fragments thereof, for use in drug screening. These may include some of the normal beta-APP isoforms (for example, of 695, 751, and 770 amino acids) or some of the familial variants of beta-APP (e.g., Swedish and/or London mutation, reviewed in Selkoe D J 1994 Annu Rev Cell Biol 10: 373–403). In addition, in vivo monitoring of epitope-tagged A-beta, beta-APP fragments, or intact epitope-tagged beta-APP may be employed using animal models that harbor a transgene. An especially preferred cell line employed in this invention is the widely available cell line HEK 293 (ATTC). A wide variety of vectors exist for the transformation of such mammalian host cells, but the specific vector used herein is in no way intended to limit the scope of the present invention. In addition to prokaryotes and mammalian host cells, eukaryotic microbes such as yeast cultures may be used.

An embodiment of the present invention provides cDNA construct that encodes for beta-APP or fragments thereof, containing an epitope tag within the A-beta sequence or the immediate flanking regions of the A-beta sequence.

Another embodiment of the present invention provides an epitope-tagged beta-APP or fragments thereof, derived from chemical synthesis or recombinant expression systems.

Another embodiment of the present invention provides for a method for detection of epitope-tagged A-beta peptide in a fluid sample in the presence or absence of beta-APP or fragments thereof, comprising: (a) capturing a soluble A-beta from the sample using a first binding substance that is a binding substance to the epitope tag; and (b) using a labeled second binding substance which binds to an epitope on a second region of the soluble A-beta other than the epitope on the A-beta which is bound by the first binding substance. In a preferred embodiment, the first binding substance is an epitope in A-beta distinct from the epitope tag and the second binding substance to the epitope tag. In a more preferred embodiment the competitive binding of a sample is determined between the first binding substance that detects the epitope tag in A-beta, and labeled epitope tagged beta-APP or fragments thereof. In a more preferred embodiment the soluble epitope-tagged A-beta is captured on a solid phase, and the capture is detected by exposing the solid phase to the labeled second binding substance to the epitope tag or other sequences in A-beta and thereafter detecting the presence of the label on the solid phase. In a more preferred embodiment the epitope tag is centered at the site between A-beta amino acid residues 16 and 17 and is a target to proteolytic cleavage and is substantially free from cross-reactivity with beta-APP and fragments thereof other than A-beta. In a more preferred embodiment the binding substances are monoclonal or polyclonal antibodies. In a more preferred embodiment, one of the binding substances is specific for neo-epitope(s) generated in the N-terminus of A-beta upon action of beta secretase(s). In a further preferred embodiment, one of the binding substances is specific for neo-epitope(s) generated in the C-terminus of A-beta upon action of gamma secretase(s) and can differentiate between A-beta 40 and A-beta 42. In a further preferred embodiment the epitope tagged beta amyloid precursor fragments are present in culture medium, or blood, cerebral spinal fluid, urine, peritoneal fluid, or tissue extracts of organism harboring the epitope tagged beta-APP.

Another embodiment provides a method of screening compounds to identify A-beta production modulators, comprising: (a) culturing cells expressing epitope tagged beta-APP or fragments thereof under conditions which result in secretion of a soluble epitope-tagged fragment of beta-APP; (b) exposing the cells to a test compound; and (c) detecting the amount of the soluble epitope-tagged beta-APP fragments present in solution, wherein an altering in the amount of the soluble beta-APP fragment in solution is compared to the amount of soluble beta-APP fragment present when the cells are not exposed to the compound indicates that the compound is an A-beta production modulator. In a preferred embodiment the cells are cultured human embryonic kidney 293 cells or derived from an organism expressing epitope tagged beta-APP or fragments thereof. In a preferred embodiment, the test compound is exposed at a concentration from 1 pM to 1 mM. In a preferred embodiment the test compound is a small molecule. In a preferred embodiment the test compound is a biological polymer. In a further preferred embodiment, the assay can detect specific inhibitors of beta-APP at position 1, 40, and 42 of the A-beta sequence.

Another embodiment of the present invention provides an in vitro method to identify beta amyloid processing activities, comprising: (a) incubation of epitope-tagged beta-APP or fragments thereof with a source of processing activities; and (b) detecting the amount of proteolytic processing by methods as outlined above. In a preferred embodiment, the method is employed to enrich or purify beta amyloid processing activities. In a preferred embodiment, the source of processing activities is cultured cells, tissue or tissue extracts.

Another embodiment of the present invention provides an in vitro method to identify beta amyloid processing activities, comprising: (a) incubation of epitope-tagged beta-APP or fragments thereof with a source of processing activities; and(b) detecting the amount of proteolytic processing by immunoblotting.

A preferred embodiment of the above methods is where the epitope tag is located within mutant forms of beta-APP or splice variants of beta-APP.

Preferred embodiments of the invention were chosen for the purpose of illustration and description, but are not intended in any way to restrict the scope of the invention.

The invention can be further understood by the following examples in which parts and percentages are by weight unless otherwise indicated. The examples presented below are provided as a guide to the practitioner of ordinary skill in the art, and are not to be construed as limiting the invention in any way.

EXAMPLE 1

Figure 1:
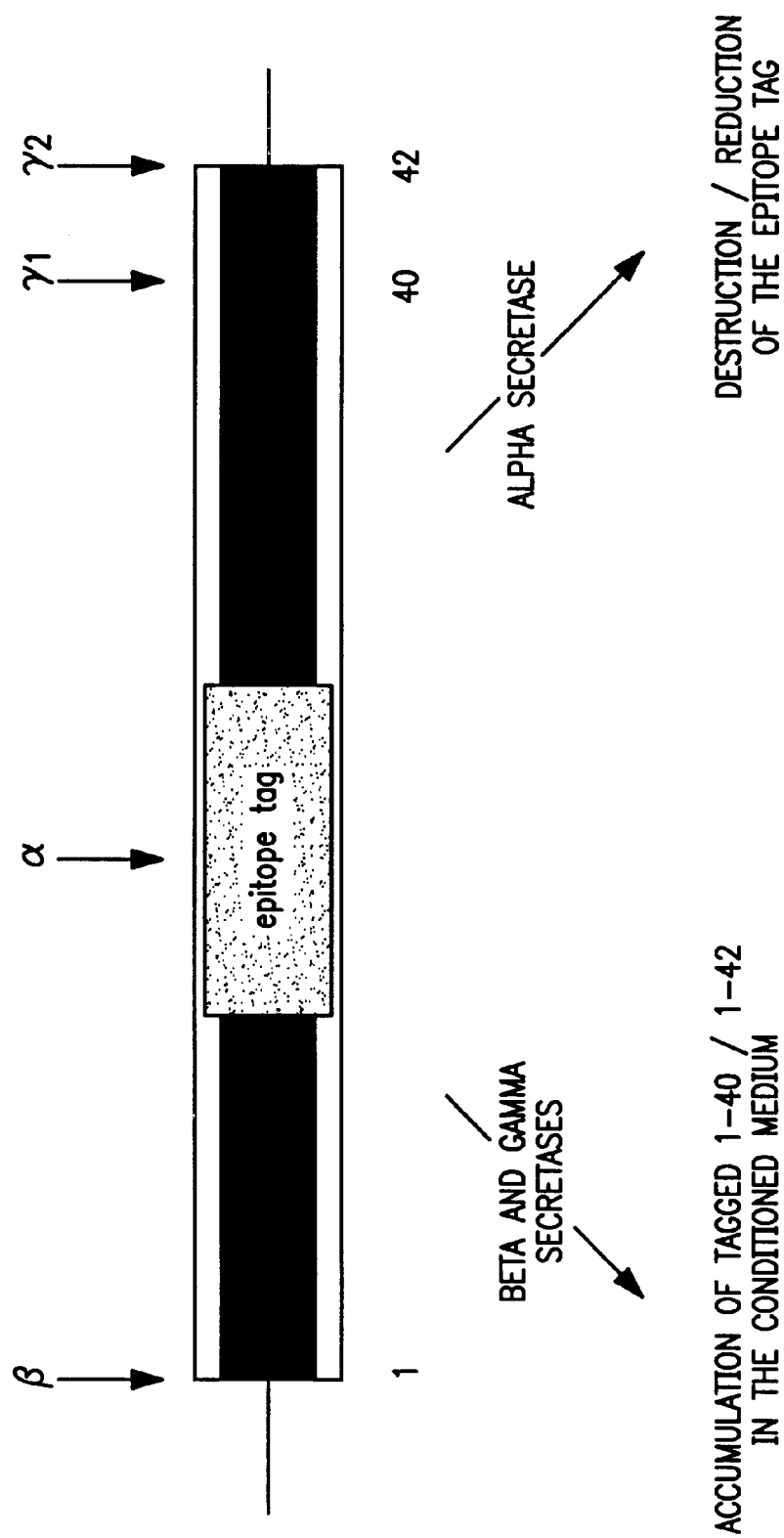
FIG. 1 Shows a possible location of an epitope tag in the A-beta sequence of the beta-APP and predicted accumulation of epitope tagged cleavage fragments. The A-beta fragment (1–42), with the proposed proteolytic cleavage sites for secretases (alpha-, beta-, gamma 1 [40]-, and gamma 2 [42]), is indicated. The epitope tag in this example is centered on the alpha secretase site (amino acids 16 to 17 in A-beta). Cleavage by beta and gamma secretases is expected to lead to an accumulation of epitope tagged A-beta (1–40) and A-beta (1–42) in the conditioned medium, whereas cleavage by alpha secretase (within the epitope tag) is expected to destroy or reduce the accumulation of epitope tagged A-beta fragments in the conditioned medium.
Figure 2:
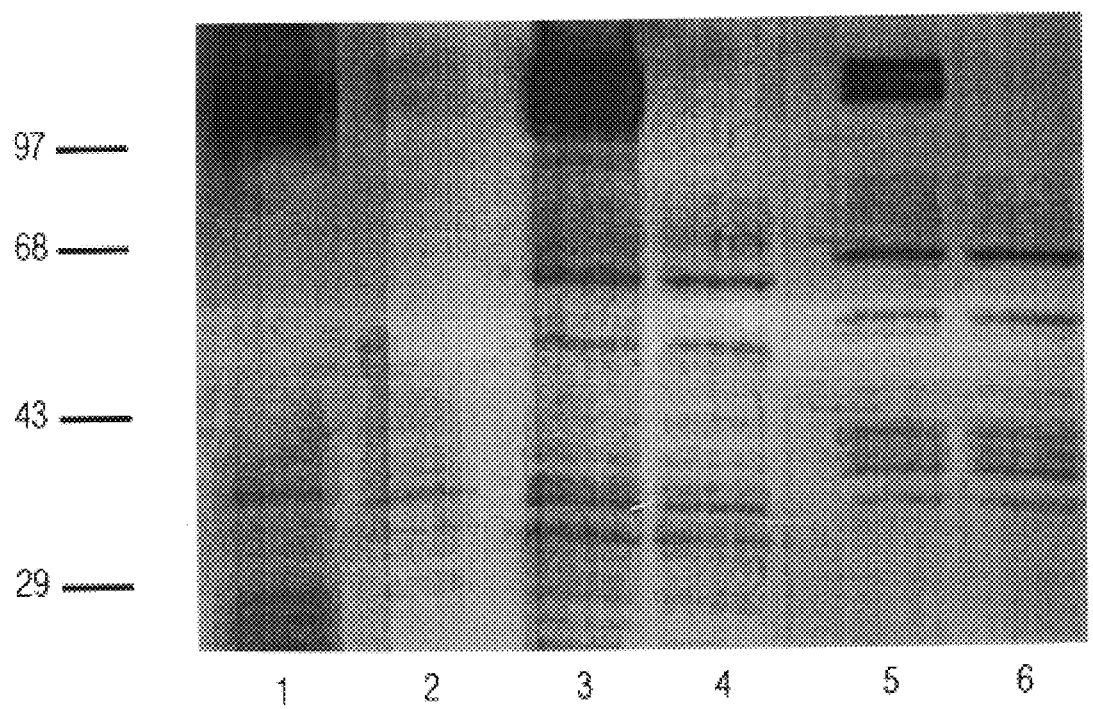
FIG. 2 Shows an immunoblot analysis of HEK 293 (human embryonic kidney cell line, ATTC #CRL-1573) cell lysates after transfection with epitope-tagged beta-APP. Cell lysates were prepared by lysis of HEK 293 cells into SDS and were fractionated by SDS-PAGE, followed by transfer to nitrocellulose membranes. The membranes were developed with mAB 22C11 (epitope in the N-terminus of full-length beta-APP; lanes 1 and 2), mAB anti-HA 11 (influenza hemagglutinin epitope: YPYDVPDYA) (SEQ ID NO: 6) (directed to the HA 11 epitope tag; lanes 3 and 4), and mAB 9E10 (directed to the myc epitope tag; lanes 5 and 6). Lane 1, HEK 293 cells transfected with HA 11 beta-APP 695; lane 2, HEK 293 cells transfected with vector alone ('Mock-transfection'); lane 3, HEK 293 cells transfected with HA 11 beta-APP 695; lane 4, HEK 293 cells transfected with vector alone; lane 5, HEK 293 cells transfected with myc beta-APP 695; lane 6, HEK 293 cells transfected with vector alone. The relative mobility of molecular weight standards is indicated to the left.
Figure 3A:
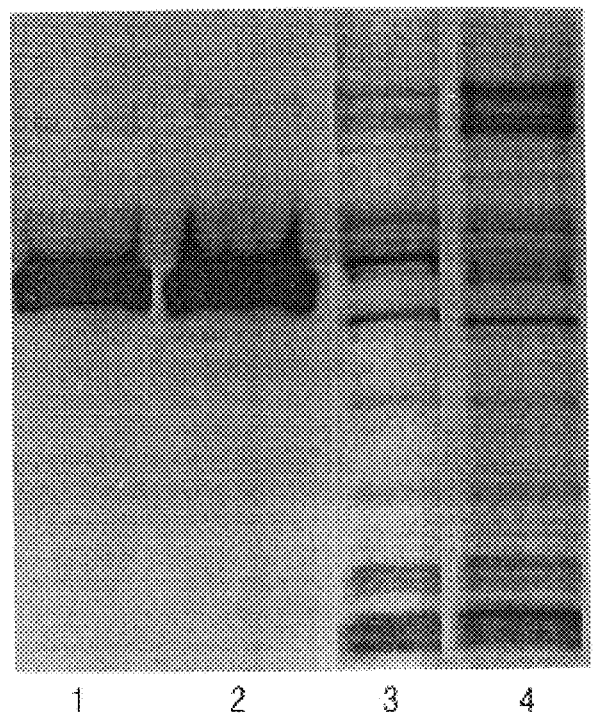
FIG. 3 Shows an accumulation of beta-APP fragments into HEK 293 conditioned medium. The 24 hour serum-free conditioned medium (lanes 1 and 2) or cell lysates (lanes 3 and 4) of HEK 293 cells transfected with vector alone (lanes 1 and 3) or HA 11 beta-APP 695 (lanes 2 and 4) were harvested. The resulting polypeptides were fractionated by SDS-PAGE (10% acrylamide in separating gel) and transferred to nitrocellulose membranes. Panel A was developed with mAB anti-HA 11, whereas panel B was developed with mAB 22C11. The relative mobility of molecular weight standards is indicated to the right.
Figure 3B:
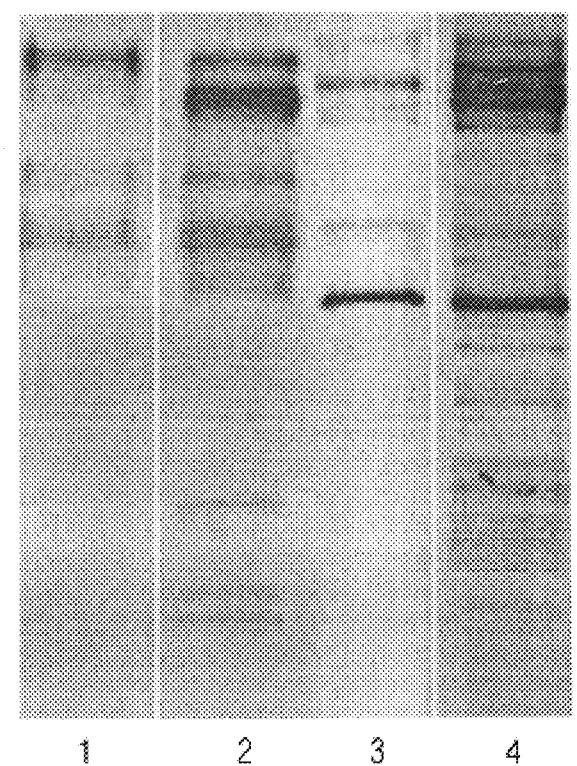

Location of an Epitope Tag in the A-beta Sequence of the Beta-APP and Expected/Predicted Accumulation of Epitope-tagged Beta-APP Cleavage Fragments The sequence of A-beta (1–42) is indicated in FIG. 1. A possible location of an epitope tag within the A-beta sequence of the beta-APP is also shown in FIG. 1. In this example, the epitope tag is centered on the alpha secretase cleavage site (indicated by alpha). In addition, the cleavage sites for beta secretase (indicated by beta, generally cleaved between −1/+1 of A-beta), and gamma 1 secretase (indicated by gamma 1, generally cleaved between 40/41) and gamma 2 secretase (indicated by gamma 2, generally cleaved between 42/43) are indicated. The numbering refers to the polypeptide sequence of the wild type A-beta polypeptide (i.e., position 1, D; position 2, A; position 3, E; position 40, V; position 41, I; position 42, A). Alternative positions of the epitope tag(s) may be throughout the A-beta sequence so long as the epitope tag does not interfere with the cellular processing of beta-APP. The predicted accumulation of epitope-tagged beta amyloid cleavage fragments with a location of an epitope tag centered on the alpha secretase site (generally cleaved between amino acids 16 and 17 of A-beta) is indicated. More specifically, cleavage by beta and gamma secretases is expected to result in the accumulation of epitope-tagged A-beta, whereas cleavage within the epitope tag by proteolytic enzyme system(s) should reduce the expression or destroy the epitope tag. An epitope tag may be introduced by replacing of existing amino acids in A-beta, by insertion of additional amino acids, or by a combination of both.

EXAMPLE 2

Immunoblotting Analysis of HEK 293 Cell Lysates After Transfection with Epitope-tagged Beta-APP Generation of cDNA constructs: Site-directed mutagenesis was utilized to incorporate the cDNA sequence for either the myc or HA 11 epitope tag within the A-beta fragment of the beta-APP (695 isoform). More specifically, the 5' primer contained the unique EcoRI sequence, followed by A-beta sequences and the epitope tag, whereas the 3' primer contained the 3' end of the beta-APP reading frame, followed by a stop codon and a XbaI cloning site. The following PCR primers were utilized: myc epitope, 5' primer: 5' GAT GCA GAA TTC CGA CAT GAC TCA GGA TAT GAA <u>GAA CAA AAA CTC ATT TCA GAA GAA GAT CTC</u> GAA GAT GTG GGT TCA AAC AAA GGT GC 3' (SEQ.ID.NO.:2) (mutated sequences underlined); HA 11 epitope, 5' primer: 5' GAT GCA GAA TTC CGA CAT GAC TCA GGA TAT GAA GTT <u>TAT CCA TAT GAT GTG CCA GAT TAT GCA</u> GAA GAT GTG GGT TCA AAC AAA GGT GC 3' (SEQ.ID.NO.:3) (mutated sequences underlined); 3' primer (for both constructs): 5' AGC TTC TAG AGG TCT AGT TCT GCA TCT GCT CAA 3' (SEQ.ID.NO.:4). Using the full-length beta-APP cDNA (695 amino acids in length) as a template, the DNA fragment was amplified, restriction-digested with EcoRI and XbaI and subcloned into pUC 18. The 5' XbaI/EcoRI fragment of beta-APP was gel-isolated after restriction digestion and also subcloned into pUC 18. The full-length reading frame of the epitope-tagged beta-APP cDNA was assembled into pUC 18 from the XbaI/EcoRI 5' fragment and EcoRI/XbaI 3' fragment. The XbaI/XbaI fragment containing the beta-APP 695 cDNA was transferred into PM3AR, an eukaryotic expression vector under control of the CMV virus promoter containing the EBV oriP for episomal maintenance of the plasmid. The presence of the desired mutations was confirmed by double-stranded DNA sequencing. In addition, the myc and HA 11 epitope tags were introduced into the Swedish beta-APP mutant.

Culture of HEK 293 E and Transfection

HEK 293 E cells were maintained in DMEM (Gibco-BRL) supplemented with 10% fetal bovine serum (Hyclone FBS), 25 μg/mL penicillin, 25 μg/mL streptomycin (Gibco-BRL), and 250 μg/mL G 418 (Gibco-BRL; geneticin). Cells were transfected with the lipofectin method according to the manufacturer (Gibco-BRL Lipofectamine). One day after transfection, the conditioned medium was replaced with selective medium (media as above containing in addition 250 μg/mL hygromycin B (Boehringer Mannheim)).

Immunoblotting Analysis of HEK 293 Cell Lysates

Confluent culture of HEK 293 cells ($1 \times 10^6$ cells/cm$^2$) transfected with vector control ("mock-transfection", lanes 2, 4, and 6), myc beta-APP 695 (lane 5), or HA 11 beta-APP 695 (lanes 1 and 3) were washed with PBS, and cell lysates prepared by the addition of SDS sample buffer containing 50 mM dithiothreitol. The samples were boiled, fractionated by SDS-PAGE (10% acrylamide in the separating gel), and transferred to nitrocellulose membranes. The membranes were blocked (PBS containing 5% dry milk) and washed extensively with PBS containing 0.1% Tween-20. The membranes were incubated with mAB 22C11 (1 μg/mL in PBS/0.1% Tween-20; Boehringer Mannheim, lanes 1 and 2), mAB anti-HA 11 (1:1000 dilution of ascites in PBS/0.1% Tween-20; BABCO, lanes 3 and 4), or mAB anti-myc (clone 9E10, 1 μg/mL in PBS/0.1% Tween-20, Calbiochem, lanes 5 and 6) for 1 hour at room temperature. The membranes were washed with PBS/0.1% Tween-20, followed by incubation with sheep anti-mouse Ig (1:10,000 dilution, Amersham) and extensive washing in PBS/0.1% Tween-20. The membranes were incubated with ECL™ chemiluminescence reagent (Amersham) and exposed to X-ray film.

EXAMPLE 3

Accumulation of Beta-APP Fragments in HEK 293/HA 11 Beta-APP 695 Conditioned Medium The 24 hour conditioned medium (serum-free, $1 \times 10^6$ cells/cm$^2$) of HEK 293 cells transfected with vector alone (lane 1) or 293/HA 11 beta-APP 695 cells (lane 2) was harvested, and cell lysates derived from vector alone (lane 3) or HA 11 beta-APP 695 (lane 4) were prepared as in Example 2. The resulting polypeptides were fractionated by SDS-PAGE (10% acrylamide in the separating gel) and transferred to nitrocellulose membranes. Panel A was probed with anti-HA 11 to detect epitope-tagged beta-APP or fragments thereof, whereas panel B was developed with mAB 22C11 to detect beta-APP or fragments thereof, which span essentially the N-terminus of full-length beta-APP (the epitope of mAB 22C11 is located in the first 100 amino acids of full-length beta-APP). Note the strong signal in the conditioned medium using mAB 22C11 (panel B, lane 2), whereas little or no staining was obtained with anti-HA 11 (panel A, lane 2). In contrast, similar staining intensities were obtained in the cell lysates using either antibody (compare panels A and B, lanes 4). Taken together, these results are consistent with cleavage of the epitope tag by alpha secretase-like activities in HEK 293 cells, resulting in reduction and/or loss of the HA 11 epitope.

EXAMPLE 4

Detection of Epitope-tagged Beta-APP Fragments in HEK 293 Conditioned Medium After Transfection with HA 11 Beta-APP A synthetic HA 11 A-beta peptide with the following sequence was synthesized: NH$_2$-ASP ALA GLU PHE ARG HIS ASP SER GLY TYR GLU GLU GLN LYS LEU ILE SER GLU GLU ASP ILE GLU ASP VAL GLY SER ASN LYS GLY ALA ILE ILE GLY LEU MET VAL GLY GLY VAL VAL-COOH (SEQ.ID.NO.:5). In this peptide, the wild-type A-beta sequence is replaced, between amino acids 12 to 21, with the HA 11 epitope (i.e., TYR PRO TYR ASP VAL PRO ASP TYR ALA (SEQ.ID.NO.:6)). The resulting peptide was purified by HPLC to greater than 95% purity and dissolved in 50% DMSO/water, and stored at −80° C. prior to use.

Panel A: Immulon 2 microtiter wells were coated with mAB anti-HA 11 (5 μg/mL in PBS, 4° C., overnight), washed with PBS and blocked with 5% BSA in PBS. The peptide was diluted in PBS/0.1% BSA/0.1% Tween-20 and incubated in the wells for 2 hours at room temperature. After washing (PBS), the wells were incubated with rabbit anti-A-beta position 1 (Serotec; 5 μg/mL in PBS/0.1% BSA/0.1% Tween-20) or rabbit anti-A-beta position 40 (QCB; 5 μg/mL in PBS/0.1% BSA/0.1% Tween-20) for 1 hour at room temperature. After washing, the wells were incubated with HRP-labeled anti-rabbit IgG (Amersham; 1:1000 dilution in PBS/0.1% BSA/0.1% Tween-20) for 1 hour. The wells were washed again, and incubated with TMB substrate. The change of absorbance of duplicate wells was determined at 650 nM and results corrected for binding of antibodies to wells in the absence of peptide. The signal obtained was linear with respect to the HA 11 A-beta peptide concentration, and approached saturation at 10 ng/mL peptide. The lower detection limit for the position 40 ELISA was approximately 0.1 ng/mL HA 11 A-beta peptide.

Panel B: Confluent cultures of HEK 293/HA 11 beta-APP 695 cells were incubated in serum-free medium containing 0.2% BSA for 16 hours. At the end of the incubation period, dilutions of the conditioned medium were prepared (100%=undiluted; 10%=1:10 diluted, etc.) and HA 11 containing beta-APP fragments were quantified as in panel A. The signal decreased with increasing dilution of the conditioned medium. Note that the ratio between the position 40 and position 1 signal is similar using the purified HA 11 A-beta peptide and the conditioned medium. This observation suggests that similar amounts of A-beta N- and C-termini are present in the conditioned medium and purified system.

EXAMPLE 5

Time-course of the Accumulation of HA 11 A-beta (1–40) and (1–42) in HEK 293/HA 11 Beta-APP Conditioned Medium: The Sensitivity of the ELISA System is Sufficient for a 96-well Format HEK 293/HA 11 beta-APP 695 cells were plated in 96-well tissue culture dishes in serum-free medium containing 0.2% BSA ($1 \times 10^6$ cells/cm$^2$). The conditioned medium was harvested at the indicated times and analyzed for the presence of HA 11 A-beta position 40, as in example 4. HA 11 A-beta polypeptides ending at position 42 were detected in a similar ELISA system. Briefly, microtiter wells were coated with anti-HA 11, incubated with the conditioned medium. Bound HA 11 A-beta 42 was detected with biotin-labeled mAB 108 (specific for the neo-epitope generated upon cleavage of beta-APP by gamma 2 secretase), followed by HRP-labeled streptavidin and TMB substrate. Note that the sensitivity of the ELISA for position 40 and 42 is sufficient for a 96-well format, thus making these assays suitable for high-throughput screening. Using the purified HA 11 A-beta 1–40 peptide, the HA 11 A-beta peptide concentration in the 24 hour conditioned medium was estimated to be 0.6 ng/mL.

EXAMPLE 6

Effect of MDL 28170 and Brefeldin A on the Accumulation of Epitope-tagged Beta-APP Fragments in HEK 293/HA 11 Beta-APP Conditioned Medium HEK 293/HA 11 beta-APP 695 cells were plated at confluency ($1 \times 10^6$ cells/cm$^2$) in 96-well tissue culture dishes in serum-free medium containing 0.2% BSA in the presence of the indicated concentration of either a previously described gamma secretase inhibitor MDL 28170 (Mehdi et al 1988 Biochem Biophys Res commun 157: 1117–1123) (panel A) or Brefeldin A (panel B). After 16 hours, the conditioned medium was harvested and analyzed using the HA 11 A-beta position 40-specific ELISA. Note the decrease in the HA 11 A-beta accumulation in the presence of both brefeldin A and MDL 28170. This experiment points to the suitability of the HA 11 beta-APP 695 cells for the detection of modulators of A-beta secretion/accumulation.

EXAMPLE 7

Isolation of HA 11 A-beta from HEK 293/HA 11 Beta-APP 695 Cells

HEK 293/HA 11 beta-APP 695 cells ($1\times10^6$ cells/cm$^2$) were grown to confluency and placed in serum-free medium containing 0.2% BSA for 16 hours. The conditioned medium was harvested, cellular debris removed by centrifugation at 1,000 g for 10 minutes, and stored at −80° C. prior to use. mAB anti-HA 11 matrix (BABCO) was equilibrated in serum-free medium containing 0.2% BSA, and the conditioned medium (4 L) was passed over the column at a flow-rate of 100 mL/hour. The column was washed with serum-free medium containing 0.2% BSA, distilled water, and eluted with 5% formic acid in distilled water. The elution fractions were pooled, dried in a speed vac, resuspended with water and neutralized with Tris.

The HA 11 A-beta concentration in the starting material, flow-through, and elution fraction (after dilution to account for the concentration on the affinity column) was estimated by ELISA specific for position 40 as in Examples 4 and 5. Note that the ELISA immunoreactivity is significantly reduced by absorption of the conditioned medium to the anti-HA 11 affinity matrix and that the epitope tagged A-beta fragments can be recovered from the column.

The indicated dilutions of the elution fraction were analyzed by ELISA specific for position 1, 40, and 42 in HA 11 A-beta. Note that position 1, 40, and 42 immunoreactivity is present in the elution fraction. Moreover, while the amount of 1 and 40 immunoreactivity appears to be similar, the 42-signal is lost at a lower dilution of the conditioned medium, suggesting that the concentration of HA 11 A-beta 42 is approximately 10-fold lower than that ending at 40.

The elution fraction was fractionated by SDS-PAGE (10–20% Tris Tricine gradient gel), transferred to nitrocellulose membranes and analyzed by immunoblotting using mAB anti-HA 11. Lane 1, elution fraction; lane 2, elution fraction spiked with 50 ng HA 11 A-beta peptide; lane 3, purified HA 11 A-beta peptide; lane 4, immunoblotting of the elution fraction under omission of the primary antibody. Note that polypeptides co-migrating with the purified HA 11 A-beta peptide standard are present in the elution fraction.

What is claimed is:

1. A method of screening compounds to identify A-beta production modulators, comprising:

(a) culturing cells expressing epitope tagged beta-APP or fragments thereof, said beta-APP or beta-APP fragment containing an amino acid sequence of A-beta having an epitope tag within the A-beta amino acid sequence, under conditions which result in secretion of a soluble epitope-tagged fragment of beta-APP;

(b) exposing the cells to a test compound; and (c) detecting the amount of the soluble epitope-tagged beta-APP fragments present in solution, wherein an altering in the amount of the soluble beta-APP fragment in solution is compared to the amount of soluble beta-APP fragment present when the cells are not exposed to the compound indicates that the compound is an A-beta production modulator.

2. A method according to claim 1, wherein the cells are cultured human embryonic kidney 293 cells or derived from an organism expressing epitope tagged beta-APP or fragments thereof.

3. A method according to claim 1, wherein the test compound is exposed at a concentration from 1 pM to 1 mM.

4. A method according to claim 1, wherein the test compound is a small molecule.

5. A method according to claim 1, wherein the test compound is a biological polymer.

6. A method according to claim 1, wherein the assay can detect specific inhibitors of beta-APP at position 1, 40, and 42 of the A-beta amino acid sequence.

7. A method according to claim 1, wherein the epitope tag is located within the A-beta amino acid sequence of mutant forms of beta-APP or splice variants of beta-APP.

* * * * *

UNITED STATES PATENT AND TRADEMARK OFFICE
CERTIFICATE OF CORRECTION

PATENT NO. : 6,518,011 B1
DATED : February 11, 2003
INVENTOR(S) : Dietmar A. Seiffert and Thomas J. Mitchell It is certified that error appears in the above-identified patent and that said Letters Patent is hereby corrected as shown below:

<u>Title page,</u>
Item [73], Assignee, "Bristol-Myers Squibb Company" should read -- Bristol-Myers Squibb Pharma Company --

Signed and Sealed this

Seventeenth Day of August, 2004

JON W. DUDAS
*Acting Director of the United States Patent and Trademark Office*

SEQUENCE LISTING

```
<160> NUMBER OF SEQ ID NOS: 6

<210> SEQ ID NO 1
<211> LENGTH: 43
<212> TYPE: PRT
<213> ORGANISM: Human

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 2
<211> LENGTH: 89
<212> TYPE: DNA
<213> ORGANISM: Human

<400> SEQUENCE: 2
gatgcagaat tccgacatga ctcaggatat gaagaacaaa aactcatttc agaagaagat      60
ctcgaagatg tgggttcaaa caaaggtgc                                        89

<210> SEQ ID NO 3
<211> LENGTH: 89
<212> TYPE: DNA
<213> ORGANISM: Human influenza virus

<400> SEQUENCE: 3
gatgcagaat tccgacatga ctcaggatat gaagtttatc catatgatgt gccagattat      60
gcagaagatg tgggttcaaa caaaggtgc                                        89
```

-continued

```
<210> SEQ ID NO 4
<211> LENGTH: 33
<212> TYPE: DNA
<213> ORGANISM: Human

<400> SEQUENCE: 4
agcttctaga ggtctagttc tgcatctgct caa                                    33

<210> SEQ ID NO 5
<211> LENGTH: 40
<212> TYPE: PRT
<213> ORGANISM: Human

<400> SEQUENCE: 5

Asp Ala Glu Phe Arg His Asp Ser Gly Tyr Glu Glu Gln Lys Leu Ile
1               5                   10                  15

Ser Glu Glu Asp Ile Glu Asp Val Gly Ser Asn Lys Gly Ala Ile Ile
                20                  25                  30

Gly Leu Met Val Gly Gly Val Val
            35                  40

<210> SEQ ID NO 6
<211> LENGTH: 9
<212> TYPE: PRT
<213> ORGANISM: Human

<400> SEQUENCE: 6

Tyr Pro Tyr Asp Val Pro Asp Tyr Ala
1               5
```